(12) United States Patent
Zhang et al.

(10) Patent No.: US 11,774,309 B2
(45) Date of Patent: Oct. 3, 2023

(54) IMPLANTABLE OIL-FILLED PRESSURE SENSOR

(71) Applicant: Measurement Specialities (China) Ltd., Shenzhen (CN)

(72) Inventors: Yaxiang Zhang, Shenzhen (CN); Tinghui Felix Fu, Shenzhen (CN); Xu Liang, Shenzhen (CN)

(73) Assignee: Measurement Specialties (China) Ltd., Shenzhen (CN)

( * ) Notice: Subject to any disclaimer, the term of this patent is extended or adjusted under 35 U.S.C. 154(b) by 135 days.

(21) Appl. No.: 17/392,712

(22) Filed: Aug. 3, 2021

(65) Prior Publication Data
US 2022/0042870 A1    Feb. 10, 2022

(30) Foreign Application Priority Data
Aug. 4, 2020 (CN) .......................... 202010771339.7

(51) Int. Cl.
| G01L 19/00 | (2006.01) |
| A61B 5/03 | (2006.01) |
| G01L 19/14 | (2006.01) |

(52) U.S. Cl.
CPC ............ *G01L 19/0069* (2013.01); *A61B 5/03* (2013.01); *G01L 19/147* (2013.01); *G01L 19/148* (2013.01)

(58) Field of Classification Search
None
See application file for complete search history.

(56) References Cited

U.S. PATENT DOCUMENTS

| 4,852,466 A * | 8/1989 | Freeman ................. G01L 7/082 92/96 |
| 5,483,835 A * | 1/1996 | Ciolli ..................... G01L 9/0057 73/725 |
| 5,753,819 A * | 5/1998 | Rozgo ................. G01L 19/0084 73/706 |
| 6,224,094 B1 * | 5/2001 | Norton ............... G01G 19/4142 73/745 |
| 10,012,334 B2 * | 7/2018 | Dohi ..................... G01L 19/003 |

* cited by examiner

*Primary Examiner* — Brandi N Hopkins
*Assistant Examiner* — Nigel H Plumb
(74) *Attorney, Agent, or Firm* — Barley Snyder

(57) ABSTRACT

An implantable pressure sensor is disclosed that has a small diameter and eliminates any dead zone in the flow of the pressure transmission medium, and is thus particularly adapted for implantation. In one embodiment the pressure sensor comprises a body including a cavity for receiving a liquid, and a planar mounting surface extending in an axial direction of the body. A diaphragm is attached to the pressure sensor body for transmitting an external medium pressure to the liquid in the cavity. A pressure detection chip is mounted on the mounting surface of the pressure sensor body for detecting a pressure of the liquid within the cavity, and a circuit hoard is mounted on the planar mounting surface of the body and is electrically connected to the pressure detection chip resulting in a device of smaller diameter particularly suited for implantation.

22 Claims, 8 Drawing Sheets

IMPLANTABLE OIL-FILLED PRESSURE SENSOR

CROSS-REFERENCE TO RELATED APPLICATIONS

This application claims the benefit of Chinese Patent Application No. 202010771339.7 filed on Aug. 4, 2020 in the China National Intellectual Property Administration, the whole disclosure of which is incorporated herein by reference.

FIELD OF THE INVENTION

The present disclosure relates to a pressure sensor, and more particularly, to an oil-filled pressure sensor suitable for implantation into a human body.

BACKGROUND

An oil-filled pressure sensor typically includes a metal shell, a detection diaphragm, a detection chip and a circuit board. In the prior art, the metal shell is formed with an oil cavity extending along the axial direction thereof, and the detection chip and the circuit board are horizontally mounted on the top of the metal shell. As the horizontally mounted circuit board extends in the radial direction of the sensor, the diameter of the sensor is necessarily relatively large, usually greater than 6.9 mm, which cannot meet the requirements for a human body implant application. In addition, in the prior art, oil-filled pressure sensors contain a diaphragm welding ring, which forms a dead zone in the flow of the pressure transmission medium. This also prevents embodiments of the prior art from meeting the requirements of the medical industry.

SUMMARY

A pressure sensor according to an embodiment of the present disclosure comprises a body including a cavity for receiving a liquid, and a planar mounting surface extending in an axial direction of the body. A diaphragm is attached to the body for transmitting an external medium pressure to the liquid in the cavity. A pressure detection chip is mounted on the mounting surface of the body for detecting a pressure of the liquid within the cavity, and a circuit board is mounted on the mounting surface of the body and is electrically connected to the pressure detection chip.

BRIEF DESCRIPTION OF THE DRAWINGS

The invention will now be described by way of example with reference to the accompanying Figures, of which.

DETAILED DESCRIPTION OF THE EMBODIMENTS

Figure 1:
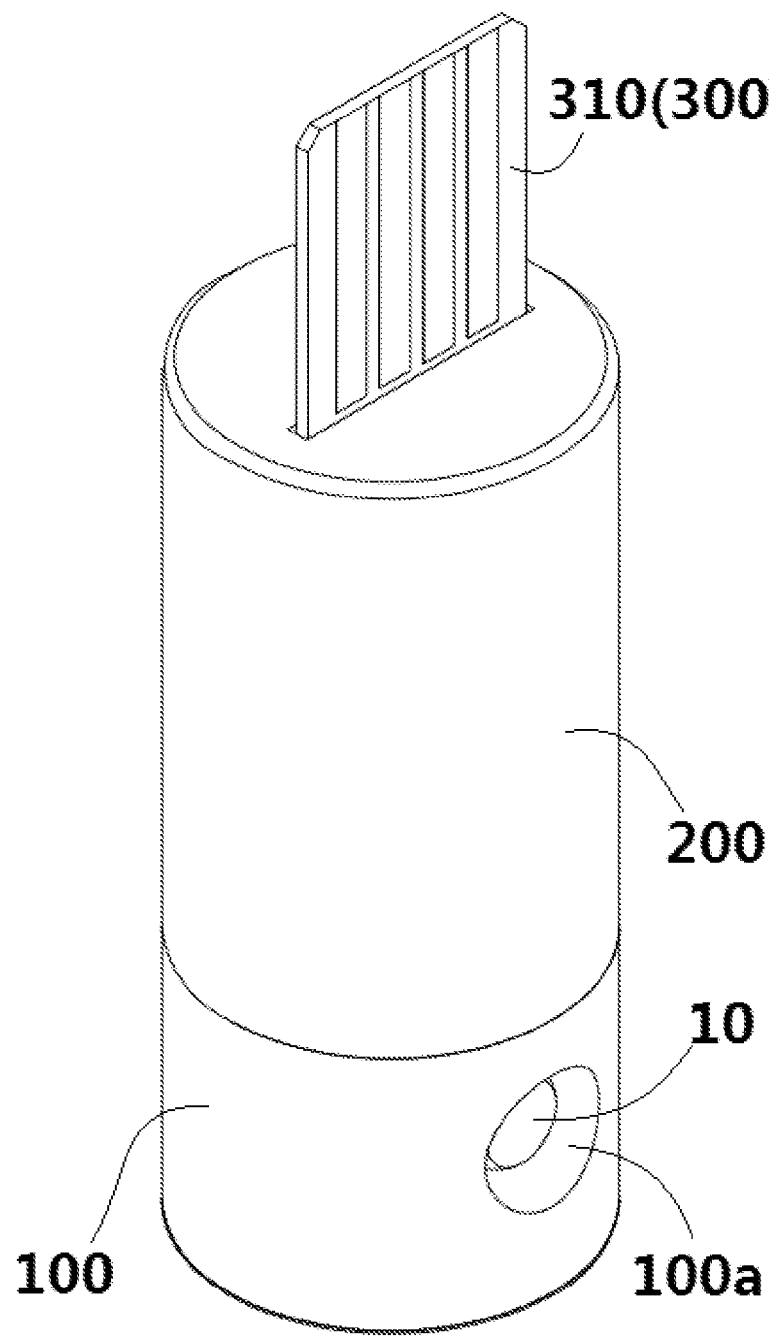
FIG. 1 schematically illustrates a perspective view of the pressure sensor according to the first embodiment of the present disclosure.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to an embodiment of the present disclosure, a pressure sensor includes a body within which a cavity 104 for receiving liquid is provided. A diaphragm is attached to the body and adapted to transmit an external medium pressure to the liquid received in the cavity 104. A pressure detection chip is mounted on the body for detecting the pressure of the liquid in the cavity 104, and a circuit board is mounted on the body and electrically connected with the pressure detection chip. A flat mounting surface is formed on the body, with the mounting surface extending along the longitudinal or axial direction of the body, and with the pressure detection chip and the circuit board mounted on the mounting surface.

Figure 2:
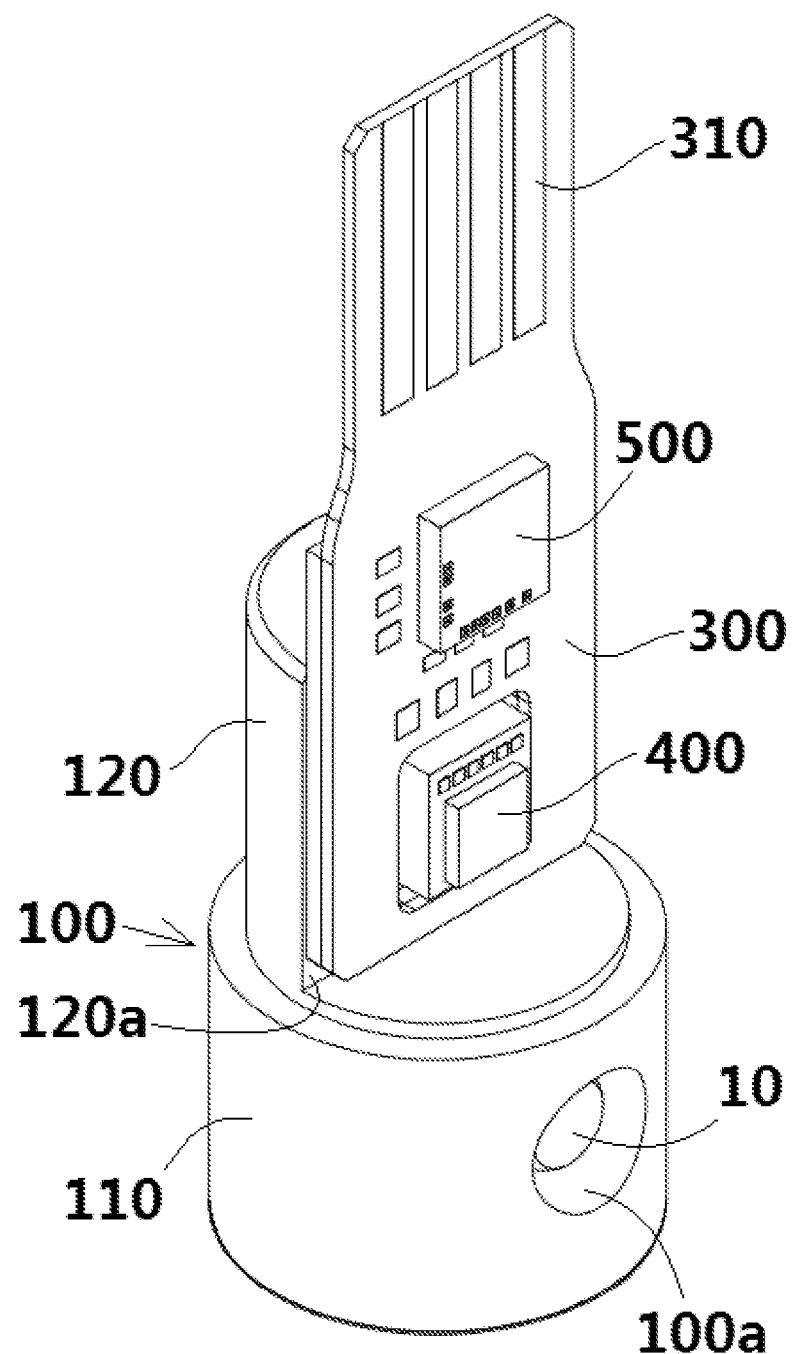
FIG. 2 illustrates the pressure sensor as shown in FIG. 1 with the cover removed.
Figure 3:
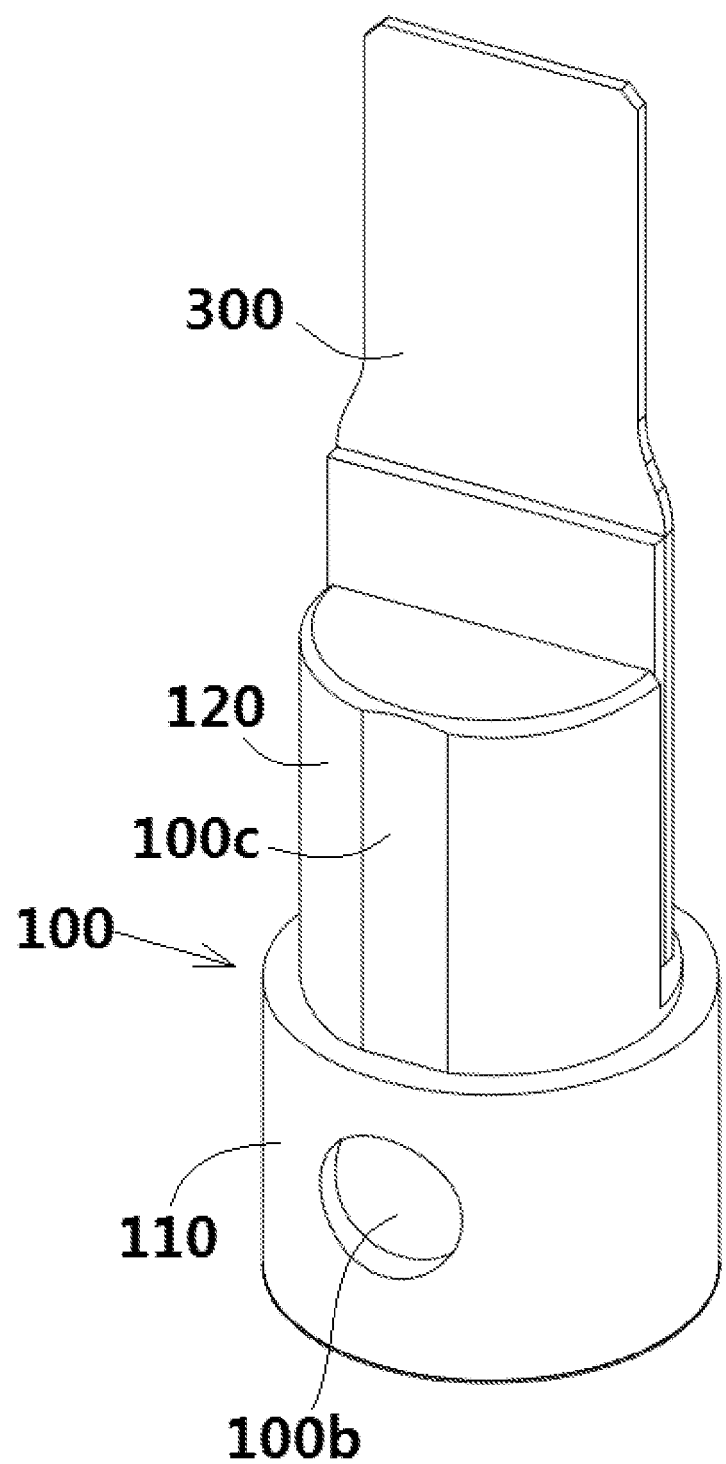
FIG. 3 schematically illustrates a side perspective view of the pressure sensor as shown in FIG. 2.
Figure 4:
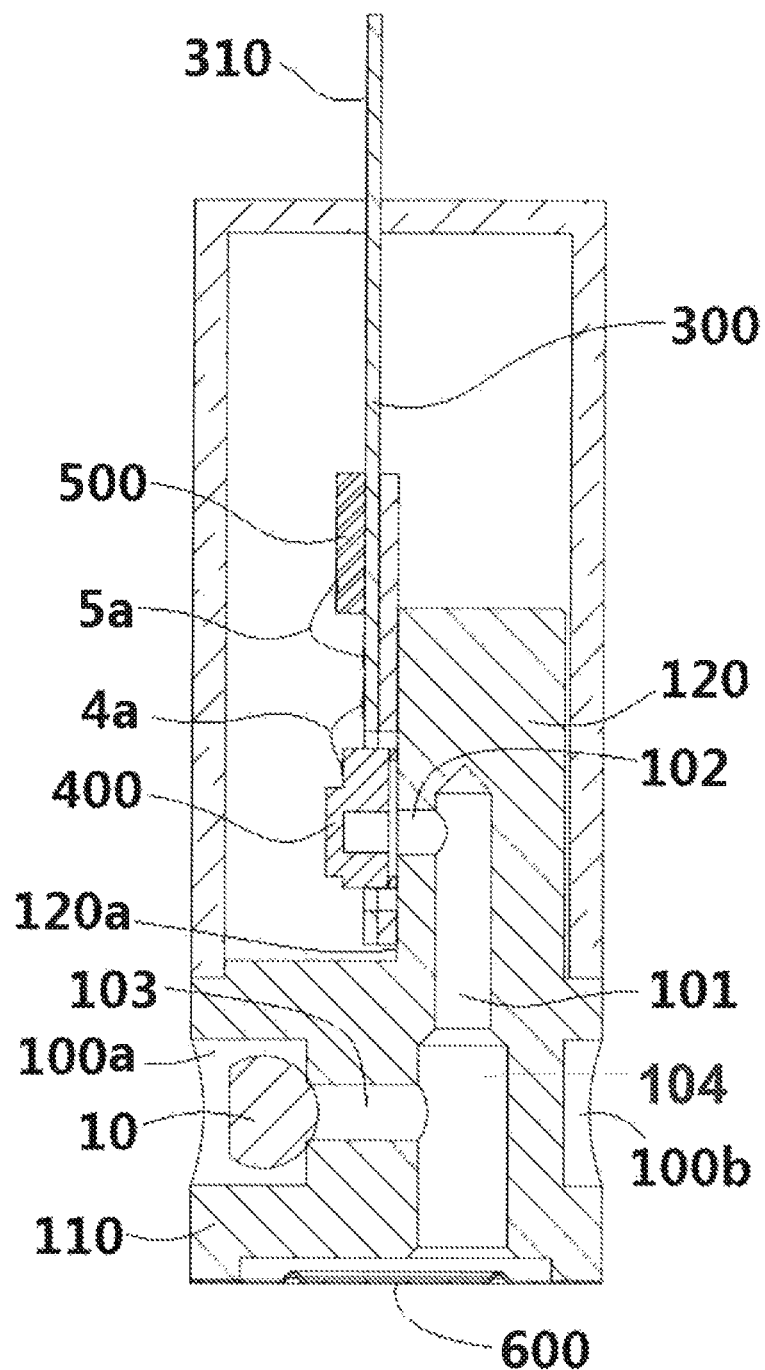
FIG. 4 illustrates a cross-sectional view of the pressure sensor as shown in FIG. 1.

FIGS. 1-4 illustrate a pressure sensor according to the first embodiment of the present disclosure. More specifically, FIG. 1 schematically illustrates a perspective view of the pressure sensor according to the first embodiment of the present disclosure. FIG. 2 illustrates the pressure sensor as shown in FIG. 1 with the cover 200 removed. FIG. 3 schematically illustrates a rear side perspective view of the pressure sensor as shown in FIG. 2. FIG. 4 illustrates a cross-sectional view of the pressure sensor as shown in FIG. 1.

As shown in FIGS. 1-4, the pressure sensor includes a body 100, a diaphragm 600, a pressure detection chip 400 and a circuit board 300. A cavity 104 for receiving liquid is formed within the body 100. The diaphragm 600, which is attached to the body 100, is adapted to transmit the external medium pressure to the liquid received in the cavity 104. The pressure detection chip 400 is mounted on the body 100 for detecting the pressure of the liquid in the cavity 104. The circuit board 300 is mounted on the body 100 and electrically connected with the pressure detection chip 400. In the exemplary embodiment, a flat or planar mounting surface 120a is formed on the body 100. The mounting surface 120a extends along the longitudinal or axial direction of the body 100. The pressure detection chip 400 and the circuit board 300 are mounted on the mounting surface 120a.

The body 100 may be a shell made of metal, and the diaphragm 600 may be a flat diaphragm made of metal. The diaphragm 600 may be directly welded to the bottom surface of the body 100 so as to seal the bottom opening of the cavity 104. The cavity 104 includes a main passage 101 extending in the axial direction of the body 100 and a first branch passage 102 extending in the radial direction of the body. The first branch passage 102 is in communication with the main passage 101, and the pressure detection chip 400 is mounted on the opening of the first branch passage.

The body 100 includes a base 110 having a cylindrical shape, and a mounting portion 120 extending upward from the top surface of the base 110. The mounting surface 120a is formed on the mounting portion 120, and the first branch passage 102 is formed in the mounting portion 120. The top surface of the base 110 extends along the radial direction of the body 100 and is perpendicular to the mounting surface 120a of the mounting portion 120. The mounting portion 120 is substantially semi-cylindrical, and the mounting surface 120a is located along the central axis of the base 110 or close to the central axis of the base 110. The radius of the mounting portion 120 is slightly smaller than the radius of the base 110, and the central axes of the mounting portion 120 and the base 110 coincide.

The pressure sensor further includes a signal processing chip 500. The signal processing chip 500 is mounted on the circuit board 300 and communicates with the pressure detection chip 400 via the circuit board 300 for processing the liquid pressure signal detected by the pressure detection chip 400, for example, for converting an analog signal into a digital signal, for amplifying or filtering the signal, or the like. The pressure detection chip 400 is electrically connected to the circuit board 300 via the first electrical connecting line 4a, and the signal processing chip 500 is electrically connected to the circuit board 300 via the second electrical connecting line 5a. In one embodiment, the pressure detection chip 400 may be a MEMS pressure detection chip, and the circuit board 300 may be a flexible circuit board. The signal processing chip 500 may be an ASIC chip.

The pressure sensor further includes a cylindrical cover 200 with a top. The cover 200 is mounted on the body 100, with the pressure detection chip 400 and the signal processing chip 500 accommodated in the cover 200. The circuit board 300 has an external plug 310, which protrudes from the top of the cover 200 so as to output the liquid pressure signal detected by the pressure sensor. The cover 200 is hermetically fitted with the body 100 and the external plug 310, such that the pressure detection chip 400, the signal processing chip 500 and the portion of the circuit board 300 other than the external plug 310 are hermetically accommodated in the cover 200.

A liquid filling port 100a is formed in the body 100 for communicating with the cavity 104, so that the liquid may be filled into the cavity 104 of the body 100 through the liquid filling port 100a. The pressure sensor further includes a sealing ball 10, which is arranged in the liquid filling port 100a for sealing the liquid filling port 100a. The sealing ball 10 may be a metal ball adapted to be directly welded to the body 100. The liquid filling port 100a is formed in the circumferential surface of the base 110, and the cavity 104 further includes a second branch passage 103 formed in the base 110 along the radial direction. The liquid filling port 100a communicates with the main passage 101 via the second branch passage 103. The central axis of the liquid filling port 100a perpendicularly intersect the central axis of the base 110 and is perpendicular to the mounting surface 120a.

A circular positioning groove 100b is formed in the peripheral surface of the base 110 opposite to the liquid filling port 100a, and a strip-shaped positioning groove 100c extending in the axial direction is formed in the peripheral surface of the mounting portion 120 opposite to the mounting surface 120a. The body 100 can be positioned in place by the circular positioning groove 100b and the strip-shaped positioning groove 100c, so as to prevent the body from moving during mounting the pressure detection chip 400 and the circuit board 300.

The cavity 104 has a bottom opening on the bottom surface of the body 100, and the diaphragm 600 may be a flat film which is directly welded to the bottom surface of the body 100 so as to seal the bottom opening of the cavity 104. As the diaphragm 600 is directly welded to the bottom surface of the body 100, there is no need to provide a welding ring, as a result the pressure sensor can be implanted in the human body as a medical pressure sensor.

In the illustrated embodiment, the pressure sensor is an oil-filled pressure sensor, and the liquid filled in the cavity 104 of the body 100 may be insulating oil, for example, insulating silicone oil. However, the present disclosure is not limited to this, and the liquid filled in the cavity 104 of the body 100 may also be other insulating liquids.

It should be understood that, as the circuit board 300 extends in the axial direction, the diameter of the pressure sensor can be reduced. For example, the diameter of the pressure sensor may be not greater than 5 mm. In this way, the pressure sensor can be implanted in the human body, for example, in a blood vessel for detecting blood pressure.

Figure 5:
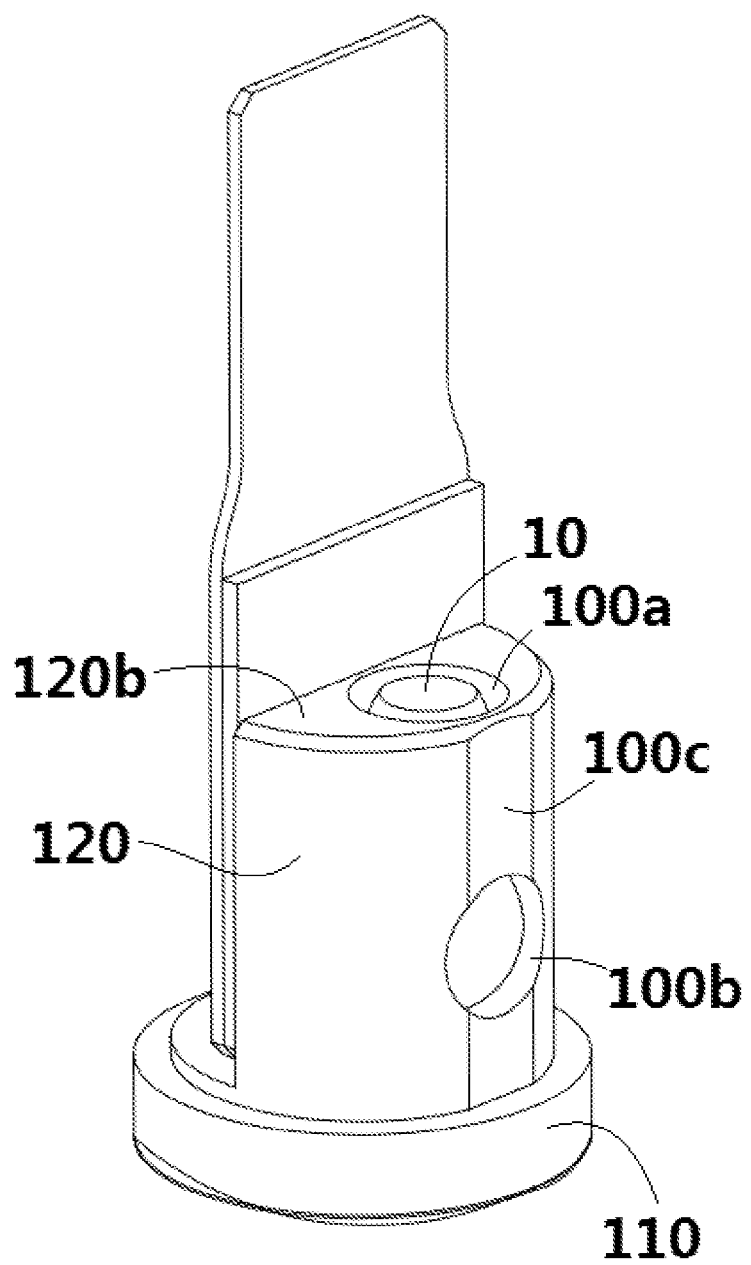
FIG. 5 schematically illustrates a perspective view of the pressure sensor according to a second embodiment of the present disclosure with the outer cover removed.
Figure 6:
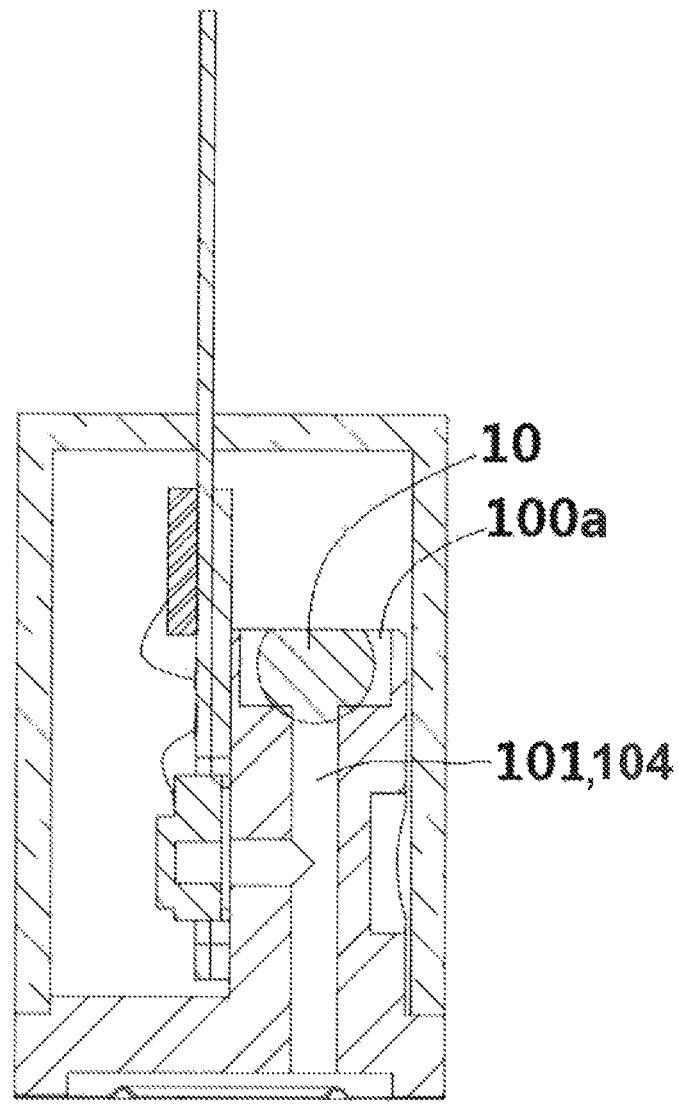
FIG. 6 illustrates a cross-sectional view of the pressure sensor according to the second embodiment of the present disclosure.

FIGS. 5 and 6 illustrate a pressure sensor according to the second embodiment of the present disclosure. More specifically, FIG. 5 schematically illustrates the perspective view of the pressure sensor according to the second embodiment of the present disclosure with the outer cover 200 removed. FIG. 6 illustrates the cross-sectional view of the pressure sensor according to the second embodiment of the present disclosure.

The main difference between the second embodiment as shown in FIGS. 5 and 6 and the first embodiment as shown in FIGS. 1-4 lies in the positions of the liquid filling port 100a and the positioning groove. Specifically, according to the second embodiment, the liquid filling port 100a is formed on the top surface of the mounting portion 120 and directly communicates with the upper end of the main passage 101, that also functions as a cavity 104. In the peripheral surface of the mounting portion 120 opposite to the mounting surface 120a, a circular positioning groove 100b and a strip-shaped positioning groove 100c extending in the axial direction through the circular positioning groove 100b are formed. The body 100 can be positioned in place by the circular positioning groove 100b and the strip-shaped positioning groove 100c, so as to prevent the body 100 from moving during mounting the pressure detection chip 400 and the circuit board 300.

Except for the above differences, other technical features of the second embodiment as shown in FIGS. 5 and 6 are substantially the same as those of the first embodiment as shown in FIGS. 1-4, which will not repeated herein for the sake of brevity.

Figure 7:
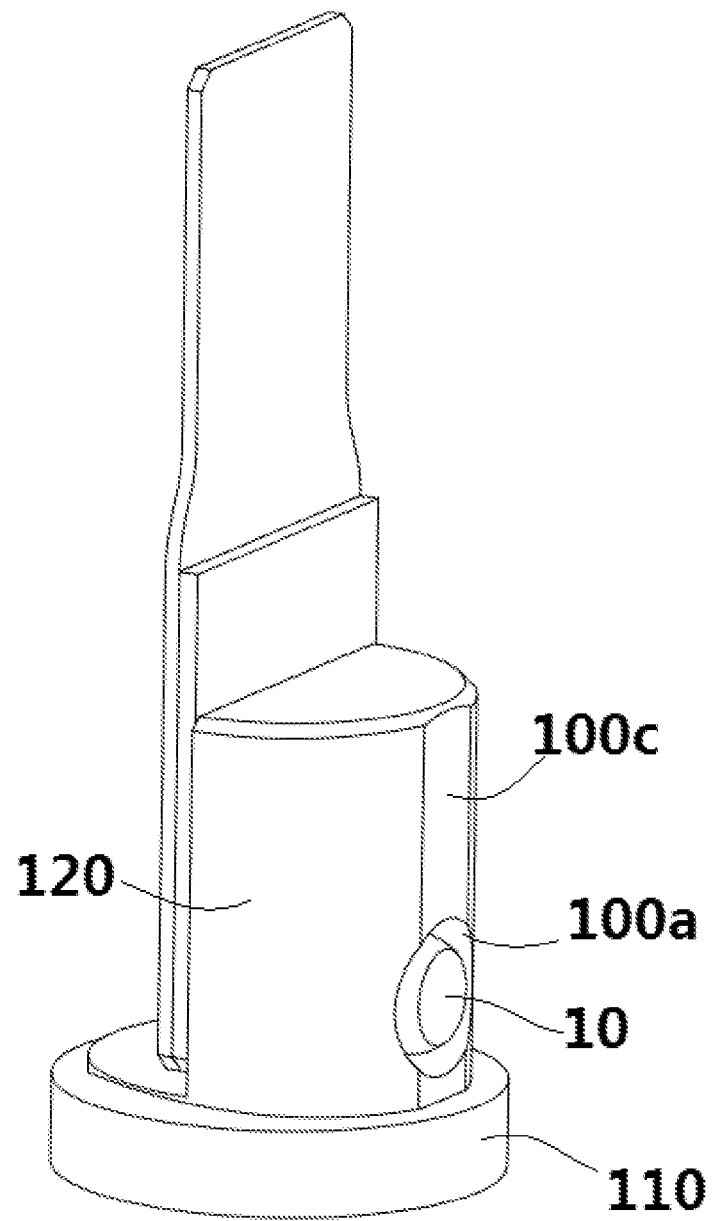
FIG. 7 schematically illustrates a perspective view of the pressure sensor according to a third embodiment of the present disclosure with the outer cover removed.
Figure 8:
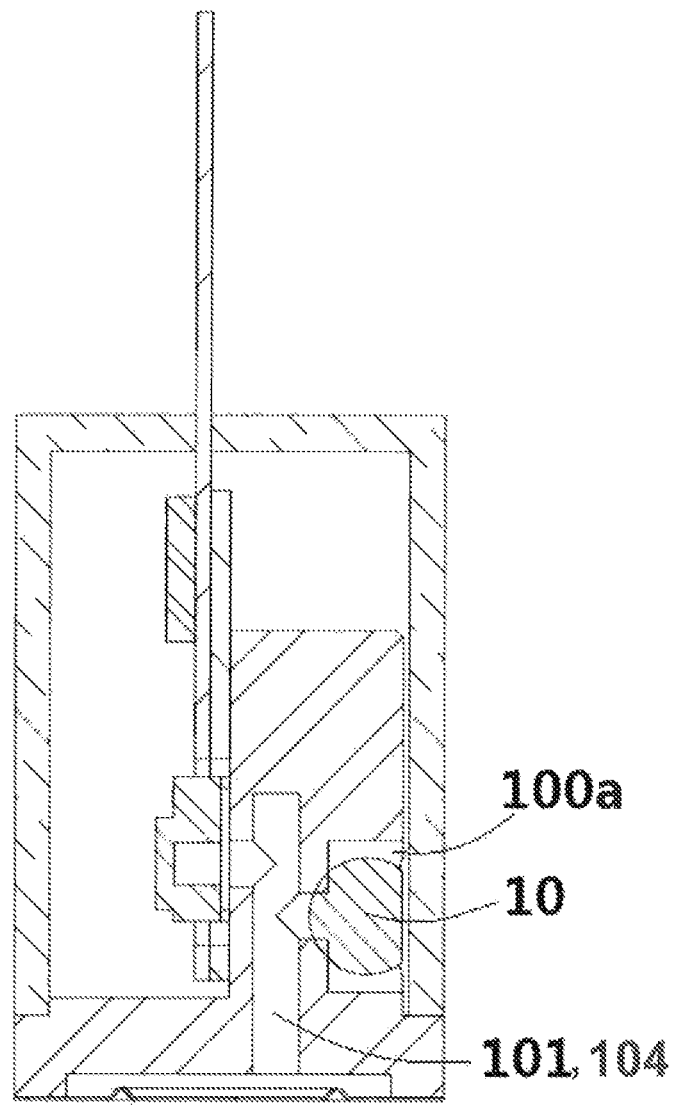
FIG. 8 illustrates a cross-sectional view of the pressure sensor according to the third embodiment of the present disclosure.

FIGS. 7 and 8 illustrate a pressure sensor according to the third embodiment of the present disclosure. More specifically, FIG. 7 schematically illustrates the perspective view of the pressure sensor according to the third embodiment of the present disclosure with the outer cover 200 removed. FIG. 8 illustrates the cross-sectional view of the pressure sensor according to the third embodiment of the present disclosure.

The main difference between the third embodiment as shown in FIGS. 7 and 8, and the first embodiment as shown in FIGS. 1-4, lies in the different positions of the liquid filling port 100a and the positioning groove. According to this third embodiment, the liquid filling port 100a is formed on the top surface of the mounting portion 120 and directly communicates with the upper end of the main passage 101, that also functions as a cavity 104. Notably, the liquid filling port 100a is formed in the peripheral surface of the mounting portion 120 opposite to the mounting surface 120a. A strip-shaped positioning groove 100c extending in the axial direction through the liquid filling port 100a is formed in the peripheral surface of the mounting portion 120 opposite to the mounting surface 120a. The liquid filling port 100a serves as a circular positioning groove, so that the body 100 can be positioned in place by the liquid filling port 100a and the strip-shaped positioning groove 100c, so as to prevent the body 100 from moving during mounting the pressure detection chip 400 and the circuit board 300.

Except for the above differences, other technical features of the third embodiment as shown in FIGS. 7 and 8 are substantially the same as those of the first embodiment as shown in FIGS. 1-4, which will not repeated herein for the sake of brevity.

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

As used herein, an element recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

What is claimed is:

1. A pressure sensor, comprising:
   a body including:
      a cavity for receiving a liquid;
      a liquid filling port formed in the body for communicating with the cavity;
      a passage formed in the body in a radial direction for providing communication between the liquid filling port and the cavity; and
      a planar mounting surface extending in an axial direction of the body;
   a diaphragm attached to the body for transmitting an external medium pressure to the liquid in the cavity;
   a pressure detection chip mounted on the planar mounting surface of the body for detecting a pressure of the liquid within the cavity; and
   a circuit board mounted on the planar mounting surface of the body and electrically connected to the pressure detection chip.

2. The pressure sensor according to claim 1, wherein the cavity defines a main passage extending in the axial direction of the body and a first branch passage extending in a radial direction of the body and in communication with the main passage, the pressure detection chip mounted on an opening of the first branch passage.

3. The pressure sensor according to claim 2, wherein the body further includes:
   a base having a cylindrical shape; and
   a mounting portion extending upward from a top surface of the base, the mounting surface formed on the mounting portion, and the first branch passage formed in the mounting portion.

4. The pressure sensor according to claim 3, wherein the base defines a top surface extending in a radial direction of the body and perpendicular to the mounting surface.

5. The pressure sensor according to claim 3, wherein the mounting portion is substantially semi-cylindrical, and the mounting surface is oriented along a central axis of the base.

6. The pressure sensor according to claim 5, wherein a radius of the mounting portion is smaller than a radius of the base, and central axes of the mounting portion and the base coincide.

7. The pressure sensor according to claim 3, further comprising a signal processing chip mounted on the circuit board, the signal processing chip in communication with the pressure detection chip via the circuit board for processing a liquid pressure signal detected by the pressure detection chip.

8. The pressure sensor according to claim 7, wherein the pressure sensor further comprises a cylindrical cover mounted on the body, the pressure detection chip and the signal processing chip being received within the cover.

9. The pressure sensor according to claim 8, wherein the circuit board includes an external plug protruding from a top of the cover for outputting the liquid pressure signal detected by the pressure sensor.

10. The pressure sensor according to claim 9, wherein the cover is hermetically sealed with the body and the external plug.

11. The pressure sensor according to claim 1, wherein the cavity has a bottom opening on a bottom surface of the body, and the diaphragm is a thin film directly welded to the bottom surface of the body so as to seal the bottom opening of the cavity.

12. The pressure sensor according to claim 1, wherein a diameter of the pressure sensor is not greater than 5 mm.

13. The pressure sensor according to claim 3, wherein the liquid filling port is formed in a peripheral surface of the base, and the cavity further includes a second branch passage formed in the base along the radial direction for providing communication between the liquid filling port and the main passage.

14. The pressure sensor according to claim 13, wherein a central axis of the liquid filling port is perpendicular to a central axis of the base and to the mounting surface.

15. The pressure sensor according to claim 14, wherein a circular positioning groove is formed in the peripheral surface of the base opposite the liquid filling port, and a strip-shaped positioning groove extending in the axial direction of the body is formed in a peripheral surface of the mounting portion opposite to the mounting surface.

16. The pressure sensor according to claim 3, wherein the liquid filling port is formed on a top surface of the mounting portion and directly communicates with an upper end of the main passage.

17. The pressure sensor according to claim 16, wherein a circular positioning groove and a strip-shaped positioning groove that extends in the axial direction through the circular positioning groove are formed in a peripheral surface of the mounting portion opposite to the mounting surface.

18. The pressure sensor according to claim 3, wherein the liquid filling port is formed in a peripheral surface of the mounting portion opposite to the mounting surface.

19. The pressure sensor according to claim 18, wherein a strip-shaped positioning groove extending in the axial direction through the liquid filling port is formed in the peripheral surface of the mounting portion opposite to the mounting surface, and the liquid filling port serves as a circular positioning groove.

20. A pressure sensor, comprising:
a body including:
a cavity for receiving a liquid;
a base having a cylindrical shape;
a mounting portion extending upward from a top surface of the base;
a planar mounting surface formed on the mounting portion, extending in an axial direction of the body; and
a liquid filling port formed in a peripheral surface of the base for communicating with the cavity;
a diaphragm attached to the body for transmitting an external medium pressure to the liquid in the cavity;
a pressure detection chip mounted on the planar mounting surface of the body for detecting a pressure of the liquid within the cavity; and
a circuit board mounted on the planar mounting surface of the body and electrically connected to the pressure detection chip,
wherein the cavity defines:
a main passage extending in the axial direction of the body and a first branch passage formed in the mounting portion and extending in a radial direction of the body and in communication with the main passage, the pressure detection chip mounted on an opening of the first branch passage; and
a second branch passage formed in the base along the radial direction for providing communication between the liquid filling port and the main passage.

21. A pressure sensor, comprising:
a body including:
a cavity for receiving a liquid wherein the cavity defines a main passage extending in the axial direction of the body and a first branch passage extending in a radial direction of the body and in communication with the main passage;
a liquid filling port formed in the body for communicating with the cavity;
a planar mounting surface extending in an axial direction of the body;
a base having a cylindrical shape; and
a mounting portion extending upward from a top surface of the base, the mounting surface formed on the mounting portion, and the first branch passage formed in the mounting portion;
a diaphragm attached to the body for transmitting an external medium pressure to the liquid in the cavity;
a pressure detection chip mounted on an opening of the first branch passage on the planar mounting surface of the body for detecting a pressure of the liquid within the cavity; and
a circuit board mounted on the planar mounting surface of the body and electrically connected to the pressure detection chip,
wherein the liquid filling port is formed on a top surface of the mounting portion and directly communicates with an upper end of the main passage.

22. A pressure sensor, comprising:
a body including:
a cavity for receiving a liquid; and
a planar mounting surface extending in an axial direction of the body;
a base having a cylindrical shape;
a mounting portion extending upward from a top surface of the base, the mounting surface formed on the mounting portion, and the first branch passage formed in the mounting portion; and
a liquid filling port is formed in a peripheral surface of the mounting portion opposite to the mounting surface for communicating with the cavity;
a diaphragm attached to the body for transmitting an external medium pressure to the liquid in the cavity;
a pressure detection chip mounted on the planar mounting surface of the body for detecting a pressure of the liquid within the cavity; and
a circuit board mounted on the planar mounting surface of the body and electrically connected to the pressure detection chip,
wherein the cavity defines a main passage extending in the axial direction of the body and a first branch passage extending in a radial direction of the body and in communication with the main passage, the pressure detection chip mounted on an opening of the first branch passage, and,
wherein a strip-shaped positioning groove extending in the axial direction through the liquid filling port is formed in the peripheral surface of the mounting portion opposite to the mounting surface, and the liquid filling port serves as a circular positioning groove.

* * * * *